United States Patent [19]
Ruckdeschel

[11] Patent Number: 6,109,479
[45] Date of Patent: Aug. 29, 2000

[54] DISPENSING DEVICE

[75] Inventor: Thomas W Ruckdeschel, Apex, N.C.

[73] Assignee: Bespak plc, United Kingdom

[21] Appl. No.: 09/242,331

[22] PCT Filed: Feb. 19, 1997

[86] PCT No.: PCT/GB97/02176

§ 371 Date: Apr. 23, 1999

§ 102(e) Date: Apr. 23, 1999

[87] PCT Pub. No.: WO98/06502

PCT Pub. Date: Feb. 19, 1998

[30] Foreign Application Priority Data

Aug. 15, 1996 [GB] United Kingdom .................. 9617148

[51] Int. Cl.$^7$ .................................................. B05B 9/08
[52] U.S. Cl. .................. 222/82; 222/153.14; 222/41; 222/336; 222/402.1
[58] Field of Search ................ 222/82, 336, 402.1, 222/41, 153.14, 43, 44, 46, 47; 604/232; 128/200.22

[56] References Cited

U.S. PATENT DOCUMENTS

| 2,605,763 | 8/1952 | Smoot | 128/73 |
| 3,334,788 | 8/1967 | Hamilton | 222/43 |
| 4,623,337 | 11/1986 | Maurice | 604/298 |
| 4,838,722 | 6/1989 | Katz | 401/101 |
| 4,962,868 | 10/1990 | Borchard | 222/49 |
| 5,104,380 | 4/1992 | Holman et al. | 222/82 |
| 5,145,094 | 9/1992 | Perlmutter | 222/153.14 |
| 5,307,953 | 5/1994 | Regan | 222/82 |
| 5,331,954 | 7/1994 | Rex et al. | 128/200.22 |
| 5,405,057 | 4/1995 | Moore | 222/153.14 |
| 5,626,566 | 5/1997 | Petersen et al. | 222/47 |

FOREIGN PATENT DOCUMENTS

| 0 385 815 | 9/1990 | European Pat. Off. . | |
| 1188881 | 3/1965 | Germany | 222/82 |
| 2245030 | of 0000 | United Kingdom . | |
| 323450 | 1/1930 | United Kingdom . | |
| 91/15303 | 10/1991 | WIPO . | |
| 92/11049 | 7/1992 | WIPO . | |

Primary Examiner—Kevin Shaver
Assistant Examiner—M A Cartagena
Attorney, Agent, or Firm—Smith, Gambrell & Russell, LLP

[57] ABSTRACT

A device for dispensing liquid medicaments in a spray form includes a container for liquid to be dispensed, an outlet nozzle which breaks up a flow of liquid under pressure into a spray, a piston for forcing liquid out of the container under pressure and through the nozzle, and a drive for moving the piston a predetermined distance to dispense a predetermined quantity of liquid from the container. A cap fits over the outlet nozzle when the device is not in use, and interengaging elements are provided on the cap and the drive to allow rotation of the drive by the cap during use of the device.

16 Claims, 4 Drawing Sheets

DISPENSING DEVICE

The invention relates to dispensing devices and particularly to dispensing devices for the dispensing liquid medicaments in a spray form.

The device may be used to dispense medicaments and is particularly suitable for nasal use.

WO-A-91/15303 discloses a dispensing device comprising a container for liquid to be dispensed, an outlet nozzle including means to break-up flow of liquid under pressure into a spray, a piston for forcing liquid out of the container under pressure and through the nozzle and drive means for moving the piston a predetermined distance to dispense a predetermined quantity of liquid from the container.

The invention provides a dispensing device comprising a container for liquid to be dispensed and initially closed at one end by a frangible seal, an outlet nozzle including means to break up a flow of liquid under pressure into a spray, a piston for forcing liquid out of the container under pressure and through the nozzle and drive means for moving the piston a predetermined distance to dispense a predetermined quantity of liquid from the container in which the nozzle includes a piercing portion extending adjacent to the frangible seal of the container, characterised in initial depression of the nozzle being used to break the seal by axial movement of the piercing portion.

The nozzle may include means initially preventing depression of the nozzle.

The device preferably includes a housing for the container and the prevention means preferably includes interengaging means on the nozzle and the housing. The interengaging means may comprise shaped slots formed in the outer wall of the housing and co-operating protrusions formed on an inner wall of the nozzle.

The device may include a cap provided for fitting over the outlet nozzle when the device is not in use and interengaging means on the cap and the drive means to allow rotation of the drive means by the cap in use of the device.

Preferably the drive means includes a plunger and an arming body for preloading the plunger, the arming body including the interengaging means for co-operation with the cap. The arming body may be located within a housing of the device with the cap fitting over an end portion of the housing to allow interengagement of the cap with the arming body, in use.

Preferably rotation of the arming body stores additional energy in a pre-loaded spring, valve means being provided for controlling the flow of liquid out of the device and operation of the valve means between a closed and open position allowing release of the additional spring energy and thereby movement of the plunger to dispense the predetermined quantity of liquid. The container may include a piston slidably located therein, the plunger acting on the piston to dispense the liquid.

In a preferred embodiment, the arming body and housing include mating ramp surfaces so that rotation of the arming body relative to the housing causes axial movement of the arming body relative to the housing.

In a further aspect of the invention, there is provided a dose counter, a housing of the device including an aperture or window through which the dose counter may be viewed, the dose counter providing an indication of the number of doses remaining in the device.

Further features and advantages of the invention will be apparent from the following description, by way of example, of a preferred embodiment of the invention, the description being read with reference to the accompanying drawings, in which.

Figure 1:
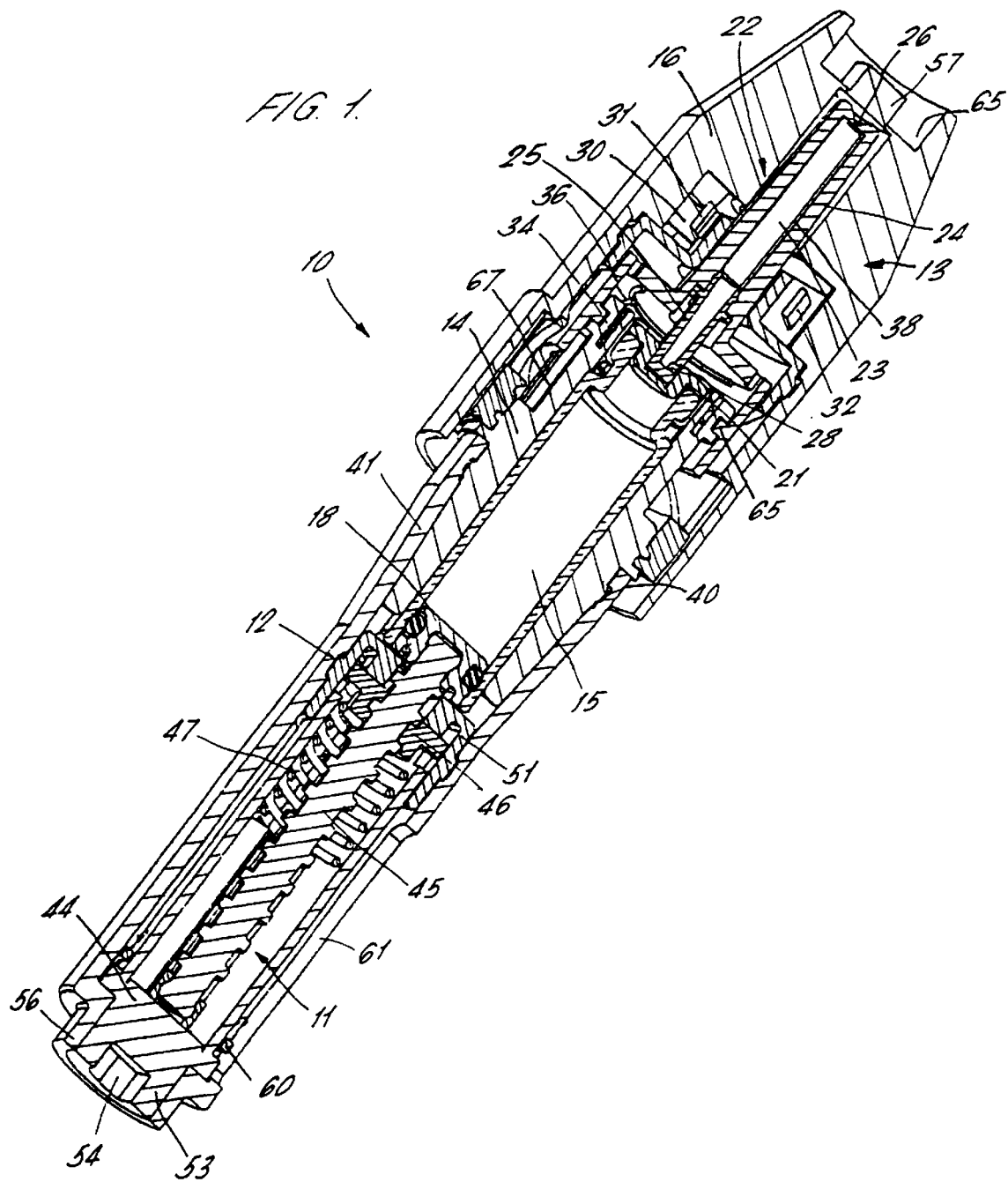
FIG. 1 is a section view through a dispensing device according to the invention.
Figure 2:
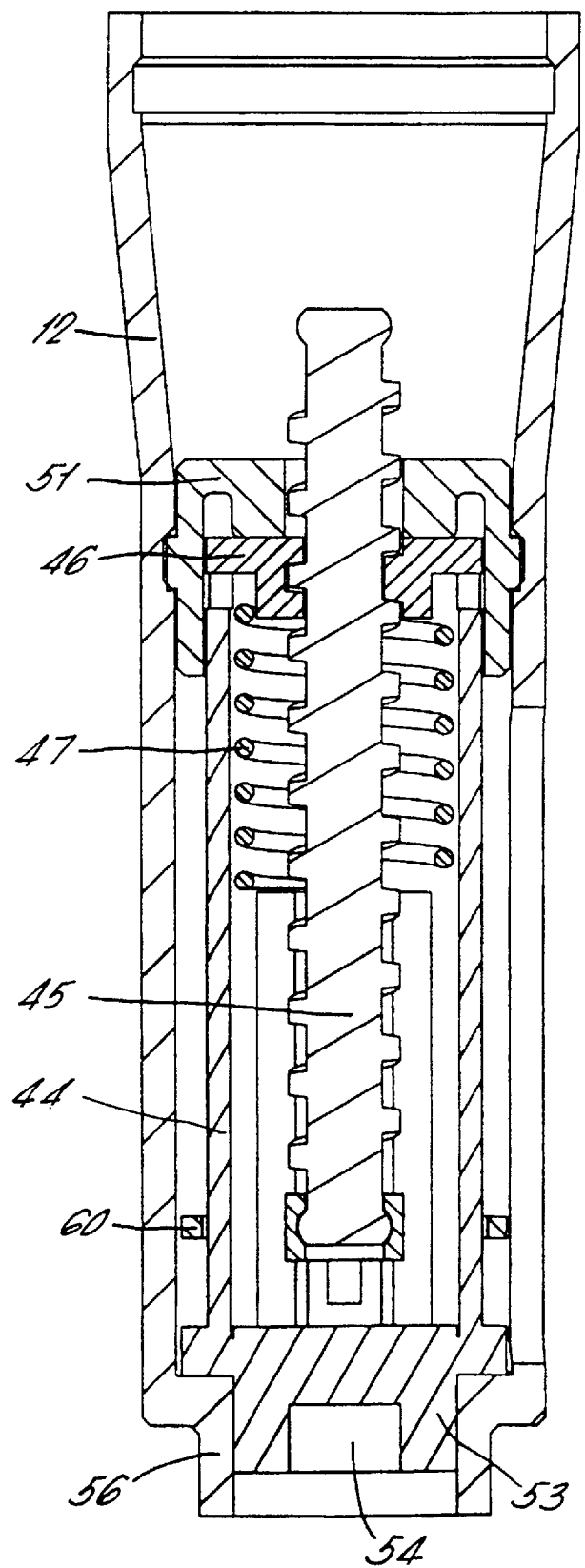
FIG. 2 is a transverse section through the lower part (drive assembly) of the device of FIG. 1.

Referring to the drawings, the main components of the dispensing device 10 are a drive assembly indicated generally by 11 which is contained within a lower housing portion 12, a valve assembly indicated generally by 13 which is contained within an upper housing portion 14, a vial 15 of medicament to be dispensed by the device and a protective cap 16.

The upper housing 14 is of generally stepped cylindrical configuration with downwardly extending legs 17 (more clearly seen in FIG. 4) and the glass vial 15 of medicament (which is also cylindrical) is located within the housing 14. The vial 15 has a piston 18 initially adjacent its lower end and in sealing contact with the inner side walls of the vial 15. The upper end of the vial is initially sealed but the frangible seal is perforated by a portion of the valve assembly 13 when the device is first used. Thus, in use, a liquid medicament stored within the vial 15 may flow outwardly through the valve 13 under the action of piston 18.

The valve assembly 13 includes a valve element 21 which is immediately adjacent the upper end of vial 15, and a nozzle assembly 22 consisting of inner and outer nested components 23, 24 which define between them a flow passage for fluid extending upwardly through the nozzle and terminating in a spray pattern block at the outward end of the nozzle 26. The lower end of inner nested component 23 abuts a valve core 25 which includes a side opening orifice 28 which is normally in sealing contact with valve member 21 but is unsealed by depression of the nozzle assembly 22 to open the side passage into the vial of medicament and allow medicament to be dispensed. The outer component 24 includes an enlarged diameter lower cylindrical part 36.

Figure 4:
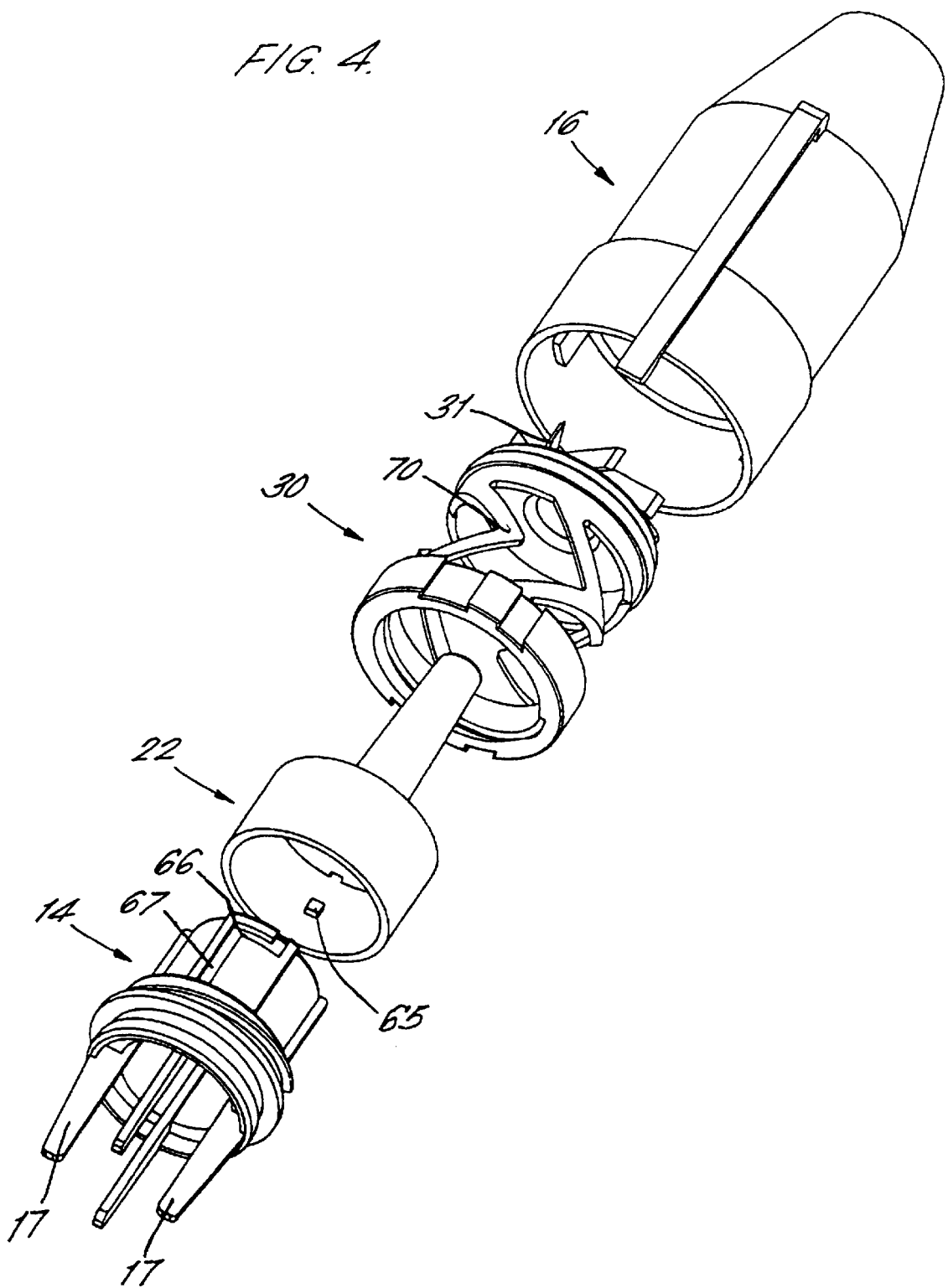
FIG. 4 is an exploded view of the upper part of the device of FIG. 1.

As most clearly shown in FIG. 4, the inner surface of cylindrical part 36 includes inwardly directed protrusions 65 (only one of which is shown in FIG. 4). These protrusions are located in and cooperate with shaped slots or tracks 66 formed in the outer surface of the upper part of upper housing 14. Thus the protrusions 65 and tracks 66 provide interengaging members on the nozzle and upper housing.

Before use of the device, the interengaging members 65, 66 are in the position shown in FIG. 1 but before the device is used, the nozzle assembly is turned through a quarter turn to move the protrusions 65 along the tracks 66. This action releases the nozzle assemble 22 allowing it to be depressed through the valve member 21 as the protrusions slide down portion 67 of tracks 66. The first depression of the nozzle assembly is then used to prime the device, the action of depressing the nozzle assembly causing the lower end of valve core 25 to perforate the frangible seal of vial 15 and allow fluid communication between the vial and the valve assembly. In use, the nozzle assembly is depressed against the action of a return spring 34 and the outer nested component 24 with its cylindrical housing portion 36 is retained connected to the upper end of upper housing 14 by the protrusions 65 engaging tracks 66.

As mentioned above, the nozzle assembly 22 is of the type designed to dispense a pressurised liquid passing through the nozzle in the form of a spray. The inner nested component 23 is cylindrical over most of its length and extends coaxially within the outer nested component 24.

Inner component 23 includes an axially extending groove 38 which is overlaid by the outer nested component to define a flow path along the length of the inner component 23. As mentioned above, the flow path communicates between a pattern block formed in the upper end of inner component 23, the pattern block being located immediately below outlet orifice 26 of the nozzle assembly. At its lower end, the groove 38 communicates with the side opening orifice 28 in the valve core 25.

The drive assembly 11 for the device is contained within lower housing 12, the lower housing 12 being fixedly attached to upper housing 14 by way of a snap-fit connection at 40. The lower housing 12 is generally cylindrical and includes a flared portion 41 at the upper end, the upper housing 14 extending within that flared portion.

The main components of the drive assembly 11 are an arming body 44, a plunger 45, a drive gear or nut 46 and a spring 47 extending between a portion of the arming body 44 and the nut 46. The purpose of the drive assembly is to cause the plunger 45 extending from one end of the drive assembly to move axially out of the housing 12 by a fixed incremented distance. Axial movement of the plunger 45 by said fixed distance causes the piston 18 to move by the same distance and expel a predetermined dose of liquid medicament from vial 15 when the valve assembly 13 is operated to allow the medicament to be dispensed.

The plunger 45 has an integrally formed thread of large lead angle which cooperates with the nut 46 which has a corresponding internally formed screw thread. The arming body 44 is used to rotate the plunger 45 in order to advance it through the nut 46 in a manner which will be described below. Immediately above the nut 46 in the assembly is a retaining washer 51 which is non-rotatably fixed to housing 12 to ensure that the vial 15, plunger 45 and other components above washer 51 do not rotate as the arming body and nut 46 are rotated.

At its lower end, the arming body has a cylindrical extension 53 which includes an internal female key 54. This is shaped to cooperate with a male key 57 formed on the cap 16. The cylindrical extension 53 of arming body 44 is axially contained within a corresponding stepped cylindrical portion 56 of housing 12. A dose counter 60 in the form of a washer extending around arming body 44 is provided and is moved axially along arming body 44 as the arming body is rotated during successive operations of the device. The dose counter 60 is visible through a cutaway side portion 61 of housing 12 to allow a visible readout of the number of doses which have been dispensed from the device.

Figure 3:
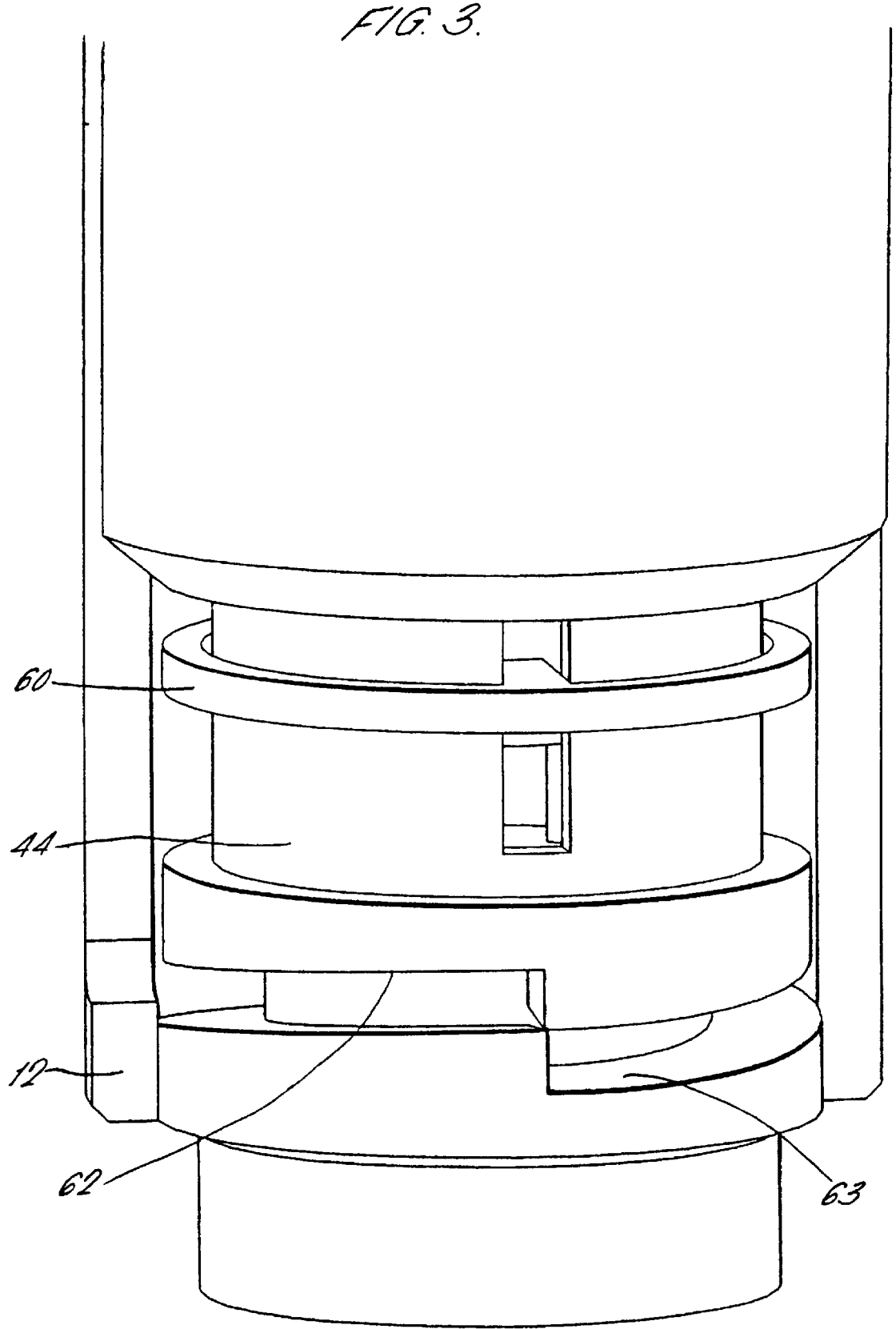
FIG. 3 is an enlarged view of the lower end portion of the drive assembly of the device of FIGS. 1 and 2.

As can be seen most clearly from FIG. 3, the cooperating surfaces between arming body 44 and the inner portion of housing 12 are not flat but include corresponding ramped portions 62, 63. The purpose of these ramped portions is to ensure that, as arming body 44 is rotated, there is axial movement of the arming body relative to housing 12, this axial movement continuing as one ramp surface passes over the other ramp surface and concluding when the surfaces reach the position shown in FIG. 3 at which point the arming body will drop into contact with the inner surface of housing 12. The effect of this cooperation of the ramp surfaces is to provide an audible and tactile click when the arming body is rotated. A secondary advantage of this arrangement is that it prevents improper rotation of the arming body relative to the housing 12 during arming of the device.

The cap 16 of the device fits over the upper portion of nozzle assembly 22, valve assembly 13 and extends around upper housing 14 to a position adjacent the mating engagement point 40 of the two housings. The inner surface of cap 16, as can be seen in FIG. 1, is shaped to fit over these components in a reasonably close fit. The cap 16 screws onto the outer part of upper housing 14 and includes an inner component 30 providing a child safety feature, known per se. This safety feature (best seen in FIG. 4) includes interengaging tabs 31 and slots 32 and plastic spring arms 70. The arrangement is such that component 30 allows removal of the cap only if the cap is simultaneously depressed relative to the housing 14 and twisted. The upper end of cap 16 includes an internal cylindrical depression 65 within which is formed male key 57.

In use of the device, the cap is first removed by pushing downwardly and twisting as described above. If the device has not previously been used, it is first primed by rotation of the nozzle assembly as described above to release the nozzle assembly and subsequent depression of the nozzle to pierce the frangible seal on vial 15. The device is then ready for operation.

In order to arm the device and prepare it to dispense a dose of medicament from vial 15, the cap 16 is used to rotate the arming body by interengagement of the male key 57 with the female key 54. The arming body is rotated through a half turn which, as described above, provides an audible and tactile click as the ramp surfaces 62, 63 move over each other. Rotation of the arming body moves the nut 46 which is keyed to the arming body against the action of spring 47. Thus, the nut 46 moves downwardly as shown in FIG. 1 through a predetermined distance fixed by the lead angle of the corresponding screw threads on the plunger 45 and within the nut 46. The spring 47 is pre-loaded to urge the nut 46 upwardly and the arming action described above compresses the spring further thus storing additional energy in the spring. At this stage, the plunger cannot move upwardly to advance the piston 18 because of the incompressable nature of the liquid within vial 15. The nozzle assembly 22 is then depressed by a user of the device, as described above, to open the valve. The plunger will then move forward with the nut 46 under the action of spring 47 to advance the piston 18 by the same predetermined distance and dispense a dose of medicament from the device.

Further doses of medicament may be dispensed in similar fashion, the upward movement of the dose counter 60 within cutaway portion 61 indicating the number of doses which have been dispensed by the device and the number remaining within the vial 15. In between uses of the device, the cap is replaced in the position shown in FIG. 1 to prevent misuse of the device.

It will be appreciated that the design of nozzle assembly 22 is such that the trapped volume within the nozzle between outlet 26 and valve number 21 is extremely small and this minimises the risk of contamination of medicament between uses of the devices.

It will also be appreciated that the recessed nature of female key 54 and the necessity for the cap i6 to fit over the housing end portion 54 to allow the male key 57 to engage the female key minimises the risk of misuse or incorrect use of the device.

What is claimed is:

1. A dispensing device (10) comprising a container (15) for liquid to be dispensed and initially closed at one end by a frangible seal, an outlet nozzle (22) including means to break up a flow of liquid under pressure into a spray, a piston (18) for forcing liquid out of the container (15) under pressure and through the nozzle (22) and drive means (11) for moving the piston (18) a predetermined distance to dispense a predetermined quantity of liquid from the container (15) in which the nozzle (22) includes a piercing portion (25) extending adjacent to the frangible seal of the container (15), characterised in initial depression of the nozzle (22) being used to break the seal by axial movement of the piercing portion (25).

2. A device (10) as claimed in claim 1, in which the nozzle (22) includes means (65, 66) initially preventing depression of the nozzle (22).

3. A device as claimed in claim 2 further comprising a housing (14) for the container (15), the prevention means comprising interengaging means (65, 66) on the nozzle and the housing (14).

4. A device (10) as claimed in claim 3 in which the interengaging means (65, 66) comprise shaped slots (66) formed in an outer wall of the housing (14) and co-operating protrusions (65) formed on an inner wall of the nozzle (22).

5. A device (10) as claimed in claim 4 in which a cap (16) is provided for fitting over the outlet nozzle (22) when the device (10) is not in use and interengaging means (54, 57) being provided on the cap (16) and the drive means (11) to allow rotation of the drive means (11) by the cap (16) in use of the device (10).

6. A device (10) as claimed in claim 5 in which the drive means (11) includes a plunger (45) and an arming body (44) for preloading the plunger (45), the arming body (44) including the interengaging means (54) for co-operation with the cap (16).

7. A device (10) as claimed in claim 6, in which the arming body (44) is located within a housing (12) of the device (10) and the cap (16) fits over an end portion of the housing to allow interengagement of the cap (16) with the arming body (44).

8. A device (10) as claimed in claim 7, in which rotation of the arming body (44) stores additional energy in a pre-loaded spring (47), valve means being provided for controlling the flow of liquid out of the device (10) and operation of the valve means (13) between a closed and open position allowing release of the spring energy and thereby movement of the plunger (45) to dispense the predetermined quantity of liquid.

9. A device (10) as claimed in claim 8 in which the plunger (45) acts on the piston (18) to dispense the liquid.

10. A device (10) as claimed in claim 9 in which the arming body (44) and housing (12) include mating ramped surfaces (62, 63) so that rotation of the arming body (44) relative to the housing (12) causes axial movement of the arming body (44) relative to the housing (12).

11. A device as claimed in claim 1 in which the container includes a piston slidably located therein and the plunger acts on the piston to dispense the liquid.

12. A device (10) as claimed in claim 2 in which the container includes a piston slidably located therein and the plunger acts on the piston to dispense the liquid.

13. A device as claimed in claim 3 in which the container includes a piston slidably located therein and the plunger acts on the piston to dispense the liquid.

14. A device as claimed in claim 6 in which the nozzle includes means intitially preventing the depression of the nozzle.

15. A device as claimed in claim 7 in which the interengaging means comprise shaped slots formed in an outer wall of the housing and co-operating protrusions formed on an inner wall of the nozzle.

16. A device as claimed in claim 8 in which the interengaging means comprise shaped slots formed in an outer wall of the housing and co-operating protrusions formed on an inner wall of the nozzle.

* * * * *

UNITED STATES PATENT AND TRADEMARK OFFICE
CERTIFICATE OF CORRECTION

PATENT NO.   : 6,109,479
DATED        : August 29, 2000
INVENTOR(S)  : Ruckdeschel Page 1 of 1

It is certified that error appears in the above-identified patent and that said Letters Patent is hereby corrected as shown below:

Title page,
Change "[22] PCT Filed: Feb. 19, 1997" to --[22] PCT Filed: Aug.12, 1997--

Signed and Sealed this

Seventeenth Day of July, 2001

*Attest:*

*Attesting Officer*

NICHOLAS P. GODICI
*Acting Director of the United States Patent and Trademark Office*